US012779250B2

(12) United States Patent
Kerns

(10) Patent No.: US 12,779,250 B2
(45) Date of Patent: Nov. 3, 2026

(54) MODULAR JIG SYSTEM

(71) Applicant: Radformation, Inc., New York, NY (US)

(72) Inventor: James Kerns, New York, NY (US)

( * ) Notice: Subject to any disclaimer, the term of this patent is extended or adjusted under 35 U.S.C. 154(b) by 1006 days.

(21) Appl. No.: 17/870,342

(22) Filed: Jul. 21, 2022

(65) Prior Publication Data

US 2024/0024703 A1 Jan. 25, 2024

(51) Int. Cl.
*A61N 5/10* (2006.01)

(52) U.S. Cl.
CPC .... *A61N 5/1075* (2013.01); *A61N 2005/1076* (2013.01)

(58) Field of Classification Search
CPC ...................... A61N 5/1075; A61N 2005/1076
See application file for complete search history.

(56) References Cited

U.S. PATENT DOCUMENTS 5,335,260 A * 8/1994 Arnold ................... A61B 6/583 378/207
5,855,582 A * 1/1999 Gildenberg ............ A61B 90/14 600/417
6,006,126 A * 12/1999 Cosman ................. A61B 34/20 600/417
6,231,231 B1 * 5/2001 Farrokhnia ............ A61B 6/583 378/207
6,315,447 B1 * 11/2001 Nord ...................... A61B 6/482 378/53
6,979,124 B2 * 12/2005 Gerwin .................. A61B 6/583 378/207
8,000,441 B2 * 8/2011 Lang ...................... A61B 6/505 378/207
2003/0004503 A1 * 1/2003 Nilsson .................. A61B 6/583 606/11
2005/0002495 A1 * 1/2005 Hein ...................... A61B 6/583 378/207
2005/0141672 A1 * 6/2005 Endo ...................... A61B 6/032 378/207
2007/0074347 A1 * 4/2007 Coppens .............. A61B 6/0442 5/600
2008/0219411 A1 * 9/2008 Gunzert-Marx ..... A61N 5/1075 250/252.1
2008/0240364 A1 * 10/2008 Main .................... A61N 5/1048 250/252.1
2008/0253506 A1 * 10/2008 Zuendorf ............... A61B 6/466 378/18
2009/0190723 A1 * 7/2009 Jang ..................... A61B 6/5276 378/207

(Continued)

*Primary Examiner* — Blake C Riddick

(57) ABSTRACT

The modular jig system may comprise a plurality of carrier jigs and an adapter jig. The plurality of carrier jigs may be operable to support and orient calibration phantoms on a treatment couch within a radiation oncology treatment vault. An individual carrier jig selected from the plurality of carrier jigs may be used to support one calibration phantom at a time. The plurality of carrier jigs may be interconnected to place and orient multiple calibration phantoms. The adapter jig may be operable to position the calibration phantoms at fixed reference locations relative to the treatment couch. The treatment couch may be positioned to image one of the calibration phantoms and the treatment couch may be repositioned such that each of the calibration phantoms may be imaged.

8 Claims, 7 Drawing Sheets

(56) References Cited

U.S. PATENT DOCUMENTS

| | | | | |
|---|---|---|---|---|
| 2010/0074414 | A1* | 3/2010 | Katsuda | G01T 1/169 378/207 |
| 2010/0266190 | A1* | 10/2010 | Zagorchev | G16H 40/63 382/131 |
| 2012/0155617 | A1* | 6/2012 | Dutta | A61B 6/583 378/207 |
| 2012/0163557 | A1* | 6/2012 | Hsieh | A61B 6/583 378/207 |
| 2012/0305793 | A1* | 12/2012 | Schiefer | A61N 5/1048 250/394 |
| 2015/0190655 | A1* | 7/2015 | Pychlau | A61N 5/1075 250/252.1 |
| 2015/0343239 | A1* | 12/2015 | Liu | A61N 5/1049 378/65 |
| 2016/0015356 | A1* | 1/2016 | Baiu | G09B 23/286 378/207 |
| 2016/0129283 | A1* | 5/2016 | Meir | A61B 6/584 348/46 |
| 2016/0278735 | A1* | 9/2016 | Franke | A61B 6/583 |
| 2017/0080254 | A1* | 3/2017 | Scheib | A61N 5/1049 |
| 2017/0184696 | A1* | 6/2017 | Zuccolotto | G01R 33/56341 |
| 2018/0140272 | A1* | 5/2018 | Ruchala | A61B 6/545 |
| 2019/0175951 | A1* | 6/2019 | Yu | A61B 6/032 |
| 2020/0179723 | A1* | 6/2020 | Gagneur | A61N 5/1075 |
| 2020/0261050 | A1* | 8/2020 | Bornefalk | A61B 6/482 |
| 2021/0370100 | A1* | 12/2021 | Yock | A61N 5/1075 |
| 2022/0203131 | A1* | 6/2022 | Wang | A61N 5/1049 |
| 2022/0219018 | A1* | 7/2022 | Yan | A61N 5/1075 |
| 2023/0036916 | A1* | 2/2023 | Stringer, III | A61B 6/583 |
| 2023/0106438 | A1* | 4/2023 | Pierre | A61B 90/39 606/117 |
| 2023/0190221 | A1* | 6/2023 | Stamm | A61B 5/055 378/207 |
| 2023/0310898 | A1* | 10/2023 | Freedman | A61N 5/1049 600/1 |
| 2023/0330437 | A1* | 10/2023 | Kerns | A61N 5/1075 |
| 2024/0066324 | A1* | 2/2024 | Alexander | A61N 5/1075 |

* cited by examiner

MODULAR JIG SYSTEM

COPYRIGHT NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever.

FIELD OF THE INVENTION

The present invention relates to the field of radiological imaging equipment, more specifically, a modular jig system for use with calibration phantoms.

BACKGROUND

A calibration phantom is a radiological imaging test object that may be placed inside of a radiation treatment vault for purposes of quality control, equipment calibration, dosimetry, and education. A medical physicist may enter the vault, position a calibration phantom, exit the vault, and perform a measurement on the calibration phantom. These steps may be repeated to image multiple, different calibration phantoms. Each iteration consumes valuable time and reduces the availability of the medical imaging system.

BRIEF DESCRIPTION OF THE DRAWINGS

Certain illustrative embodiments illustrating organization and method of operation, together with objects and advantages may be best understood by reference to the detailed description that follows taken in conjunction with the accompanying drawings in which.

DETAILED DESCRIPTION

Figure 1:
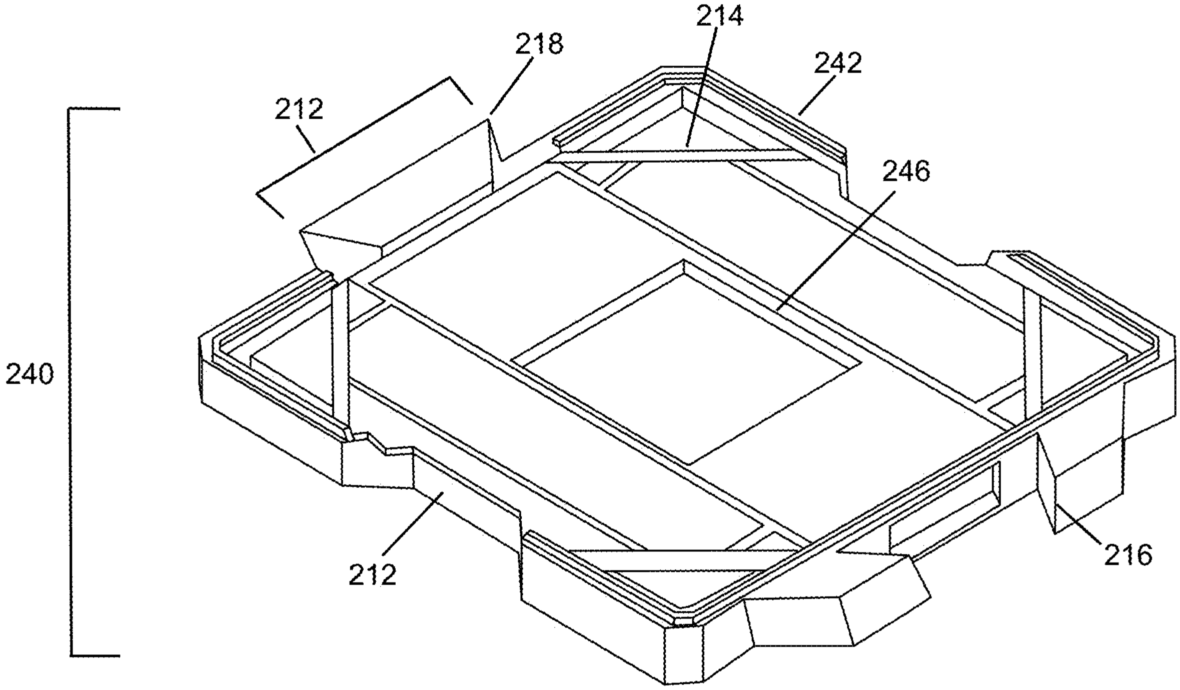
FIG. 1 is an isometric view of a multi-phantom jig consistent with certain embodiments of the present invention.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms “a” or “an”, as used herein, are defined as one or more than one. The term “plurality”, as used herein, is defined as two or more than two. The term “another”, as used herein, is defined as at least a second or more. The terms “including” and/or “having”, as used herein, are defined as comprising (i.e., open language). The term “coupled”, as used herein, is defined as connected, although not necessarily directly, and not necessarily mechanically.

Reference throughout this document to “one embodiment”, “certain embodiments”, “an embodiment” or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The modular jig system (hereinafter invention) may comprise a plurality of carrier jigs and an adapter jig. The plurality of carrier jigs may be operable to support and orient calibration phantoms on a treatment couch within a radiation oncology treatment vault. An individual carrier jig selected from the plurality of carrier jigs may be used to support one calibration phantom at a time. The plurality of carrier jigs may be interconnected to place and orient multiple calibration phantoms. The adapter jig may be operable to position the calibration phantoms at fixed reference locations relative to the treatment couch. The treatment couch may be positioned to image one of the calibration phantoms and the treatment couch may be repositioned such that each of the calibration phantoms may be imaged.

As a non-limiting example, the calibration phantoms may be objects of known density that may be used in medical imaging systems for quality control, equipment calibration, dosimetry, and education. The plurality of carrier jigs may enable medical physicists to configure and set up multiple calibration phantoms inside the radiation oncology treatment vault at one time, obviating the need to enter the radiation oncology treatment vault to position the calibration phantom, exit the radiation oncology treatment vault to initiate a measurement, and re-enter the radiation oncology treatment vault to remove a previous calibration phantom and reconfigure for a next calibration phantom. Use of the plurality of carrier jigs may save the medical physicists time and may make the medical imaging system more available for use with patients.

An individual carrier jig may be selected from the plurality of carrier jigs to comprise a base. This carrier jig may also have one or more jig-to-jig interfaces and one or more positioning elements to assist in the positioning of a calibration phantom within each carrier jig. The carrier jig forming the base may be the lowest portion of the individual carrier jig. The base, consisting of the bottom portion of the carrier jig, may contact the treatment couch when the individual carrier jig is in use. The base may stably support the individual carrier jig and the calibration phantom held securely within the individual carrier jig while in contact with the treatment couch.

The jig-to-jig interface may be configured to couple a first jig to a second jig. The first jig may be the individual carrier jig. The second jig may be selected from the plurality of carrier jigs and the adapter jig.

In some embodiments, the individual carrier jig may comprise two of the jig-to-jig interfaces such that the individual carrier jig may be operable to couple to two other jigs that are positioned on opposite sides of the individual carrier jig. The two other jigs may be selected from the plurality of carrier jigs and the adapter jig.

The jig-to-jig interfaces may define the longitudinal ends of the base. The plurality of carrier jigs may be daisy chained longitudinally along the treatment couch by interconnecting the jig-to-jig interfaces.

The jig-to-jig interface may be a coupler that mates with a corresponding coupler on another jig. As a non-limiting example, the jig-to-jig interface may be a dovetail mechanical connection such that a dovetail notch on the first jig engages a dovetail tab on the second jig to prevent the first jig and the second jig from separating. The dovetail notch may engage the dovetail tab when the dovetail tab of the second jig is lowered onto the dovetail notch of the first jig while aligning the dovetail notch and the dovetail tab, or vice versa.

The dovetail notch may be a cutout on the base that may have the shape of an isosceles trapezoid when viewed from above. The dovetail tab may be an extension of the base that may have the shape of an isosceles trapezoid when viewed from above. The dovetail notch and the dovetail tab may comprise compatible sizes such that the dovetail tab fits into the dovetail notch without requiring excessive force and without creating excessive gaps. When the dovetail notch on the first jig engages the dovetail tab on the second jig, the first jig and the second jig may not be separated except by lifting the first jig or the second jig.

The one or more positioning assistants may be mechanical features of the individual carrier jig that may be configured to support and orient the calibration phantoms. As non-limiting examples, the one or more positioning assistants may comprise physical notches, channels, apertures, tabs, armatures, dividers, or depressions that may mate with one or more features of the calibration phantoms. In some embodiments, the individual carrier jig may comprise the one or more positioning assistants that are adapted for a single calibration phantom. In some embodiments, the individual carrier jig may comprise the one or more positioning assistants that are adapted for use with one or more calibration phantoms at different times.

The plurality of carrier jigs may be made from material that is radiolucent such that the plurality of carrier jigs do not interfere with the radiological measurements of the calibration phantoms.

The plurality of carrier jigs may comprise a multi-phantom jig. The multi-phantom jig may be operable to support one calibration phantom selected from multiple calibration phantoms. The multiple calibration phantoms may be manufactured by multiple vendors. The multi-phantom jig may be operable to support calibration phantoms of various heights and widths. As non-limiting examples, the one calibration phantom supported by the multi-phantom jig may be a horizontally-oriented square plate, a cube, or a rectangular prism.

The one or more positioning assistants of the multi-phantom jig may comprise a plurality of side walls, a plurality of corner supports, and one or more central depressions. The one or more positioning assistants of the multi-phantom jig may be operable to center the individual carrier jig and/or to prevent the individual carrier jig from sliding off of the multi-phantom jig.

The plurality of carrier jigs may comprise an angled jig. The angled jig may be operable to support calibration phantoms that require being held in a vertical orientation. As non-limiting examples, the calibration phantom supported by the angled jig may be a disk or square plates of various thicknesses.

The one or more positioning assistants of the angled jig may comprise a first inclined surface and a second inclined surface. The first inclined surface and the second inclined surface may be oriented longitudinally such that the one or more positioning assistants are lowest at the center of the angled jig and increase in height moving longitudinally in either direction. In some embodiments, the first inclined surface and the second inclined surface may form a 90-degree angle such that the first inclined surface and the second inclined surface may be operable to support a square phantom in a vertical orientation.

The first inclined surface may comprise a first curved groove and the second inclined surface may comprise a second curved groove. The first curved groove and the second curved groove may be longitudinally-oriented and centered within the first inclined surface and the second inclined surface, respectively. The first curved groove and the second curved groove may be operable to support a round phantom in a vertical orientation.

The first inclined surface and the second inclined surface may comprise slide stops. The slide stops may be upward projections of the edges of the first inclined surface and the second inclined surface that may prevent the calibration phantom from sliding laterally.

The plurality of carrier jigs may comprise a Computed Tomography (CT) phantom jig. The CT phantom jig may be operable to support horizontally-oriented cylindrical calibration phantoms. As non-limiting examples, the cylindrical phantom may comprise a plurality of internal components that may vary in density. The one or more positioning assistants of the CT phantom jig may comprise a vertical support wall. The vertical support wall may be operable to support the calibration phantom via axial hooks located on the cylindrical calibration phantom. In some embodiments, the vertical support wall may comprise a centering stub that may be operable to prevent the calibration phantom from sliding off of the CT phantom jig laterally.

The adapter jig may be operable to fix the location of the plurality of carrier jigs on the treatment couch. Specifically, the adapter jig may comprise an index bar coupler located on the underside of the base of the adapter jig. The index bar coupler may be a laterally-oriented notch that is sized to engage an index bar of the treatment couch. The index bar may be a physical landmark that may be coupled to the treatment couch and may be operable to position the patient and immobilization devices. The index bar may comprise feet on each end of the index bar. The feet may engage positioning cutouts located on the sides of the treatment couch such that the index bar may be positioned laterally across the treatment couch at one of a number of predetermined positions along the length of the treatment couch.

With the index bar in place laterally across the treatment couch, the adapter jig may be placed on top of the index bar such that the index bar coupler straddles the index bar and prevents the adapter jig from shifting longitudinally along the treatment couch.

The adapter jig may comprise a handle that may rise from the center of the adapter jig. The handle may be adapted to be grasped by the medical physicist such that the adapter jig may be lifted or repositioned.

The advantages of the invention are numerous and may comprise:

The system is modular and may be configured and reconfigured for many different scenarios.

The system enables the placement of multiple calibration phantoms within the radiation oncology treatment vault at one time and thereby obviates the need for repeated trips in and out of the radiation oncology treatment vault.

The system is flexible enough to permit measurements with a single phantom supported by a single jig.

The system is flexible enough that some jigs may be operable to support more than one type of calibration phantom.

The system enables the multiple calibration phantoms to be placed in fixed position relative to each other and relative to the treatment couch.

The system is vendor agnostic and enables phantoms manufactured by multiple vendors to be measured in the same imaging session.

Turning now to FIG. 1, the figure presents a multi-phantom jig 240 consistent with certain embodiments of the present invention. In an exemplary embodiment, jig-to-jig interfaces 212 of a base 212 of the multi-phantom jig 240 comprise a dovetail notch 216 and a dovetail tab 218. The jig-to-jig interfaces 212 are couplings between multiple jigs that enable the placement of multiple interconnected phantoms on the treatment couch simultaneously. A plurality of side walls 242, a plurality of corner supports 214, and one or more central depressions 246 may support a calibration phantom, may position a calibration phantom, may prevent a calibration phantom from sliding off of the multi-phantom jig 240, or any combination thereof. The calibration phantom that is placed upon the multi-phantom jig 240 may vary greatly in width, length, height, and shape, thus providing flexibility to accommodate many phantoms from many vendors.

Figure 2:
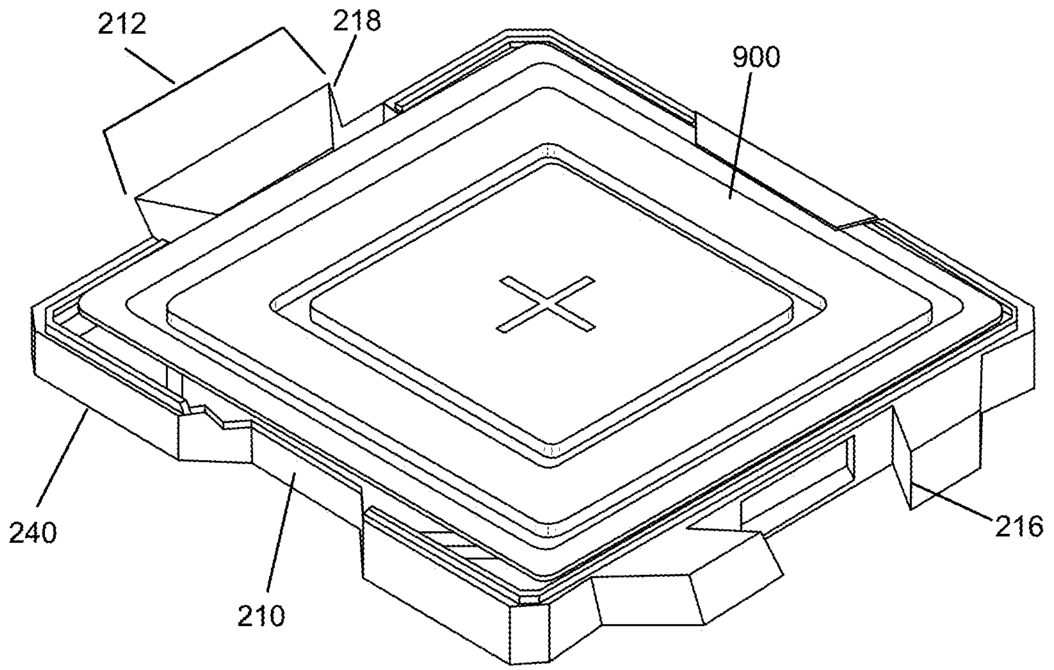
FIG. 2 is an isometric view of a multi-phantom jig consistent with certain embodiments of the present invention, illustrating a calibration phantom in place on the jig.

Turning now to FIG. 2, the figure presents a multi-phantom jig 240 with a calibration phantom 900 in place on top of the multi-phantom jig 240 consistent with certain embodiments of the present invention. In an exemplary embodiment, the calibration phantom 900 is a horizontally-oriented square disk. Jig-to-jig interfaces 212 of a base 210 of the multi-phantom jig 240 comprise a dovetail notch 216 and a dovetail tab 218. The jig-to-jig interfaces 212 are couplings between multiple jigs that enable the placement of multiple interconnected phantoms on the treatment couch simultaneously.

Figure 3:
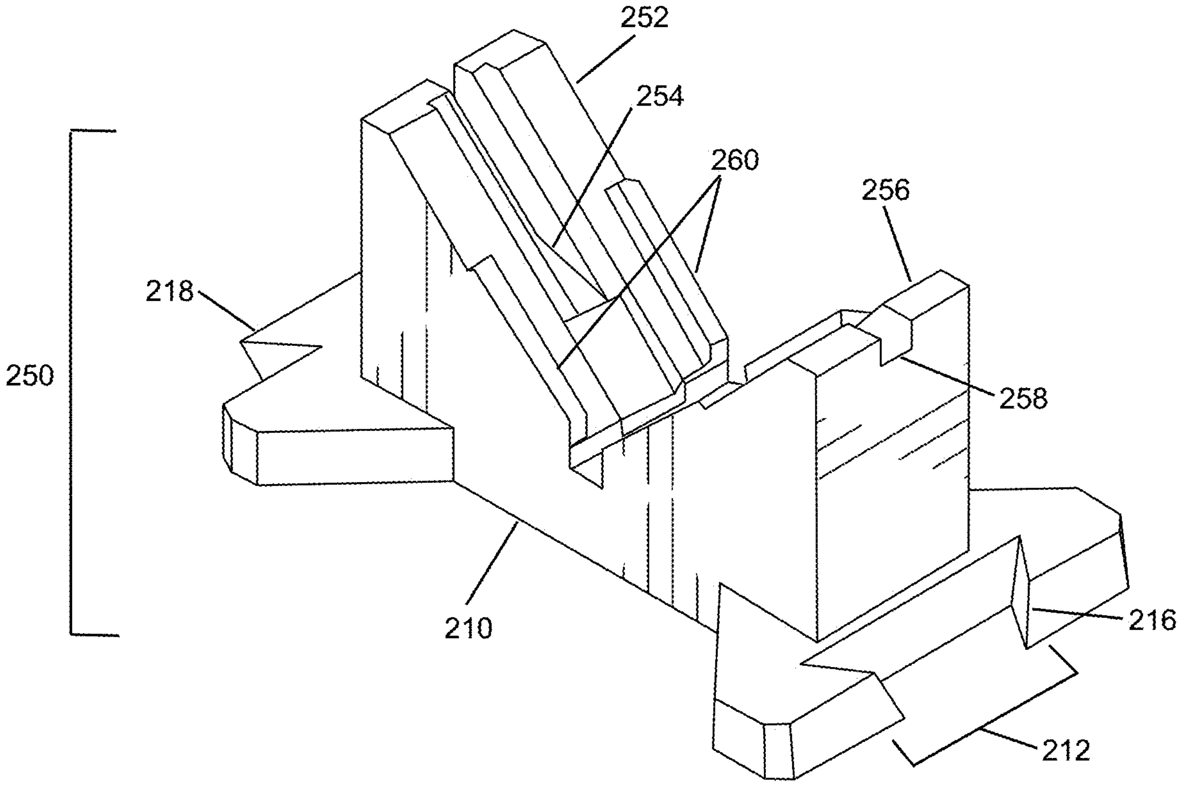
FIG. 3 is an isometric view of an angled jig consistent with certain embodiments of the present invention.

Turning now to FIG. 3, the figure presents an angled jig 250 consistent with certain embodiments of the present invention. In an exemplary embodiment, jig-to-jig interfaces 212 of a base 210 of the angled jig 250 comprise a dovetail notch 216 and a dovetail tab 218. The jig-to-jig interfaces 212 are couplings between multiple jigs that enable the placement of multiple interconnected phantoms on the treatment couch simultaneously. A first inclined surface 252 and a second inclined surface 256 slope upwards in opposite directions from the center of the angled jig 250 forming a right angle such that square calibration phantoms may be retained in a vertical orientation by the jig. Slide stops 260 may prevent the calibration phantom from sliding off of the angled jig 250 in a lateral direction. The first inclined surface 252 comprises a first curved groove 254 and the second inclined surface 256 comprises a second curved groove 258 such that a disk-shaped calibration phantom may be retained in a vertical orientation on the angled jig 250 by placing the phantom into the grooves.

Figure 4:
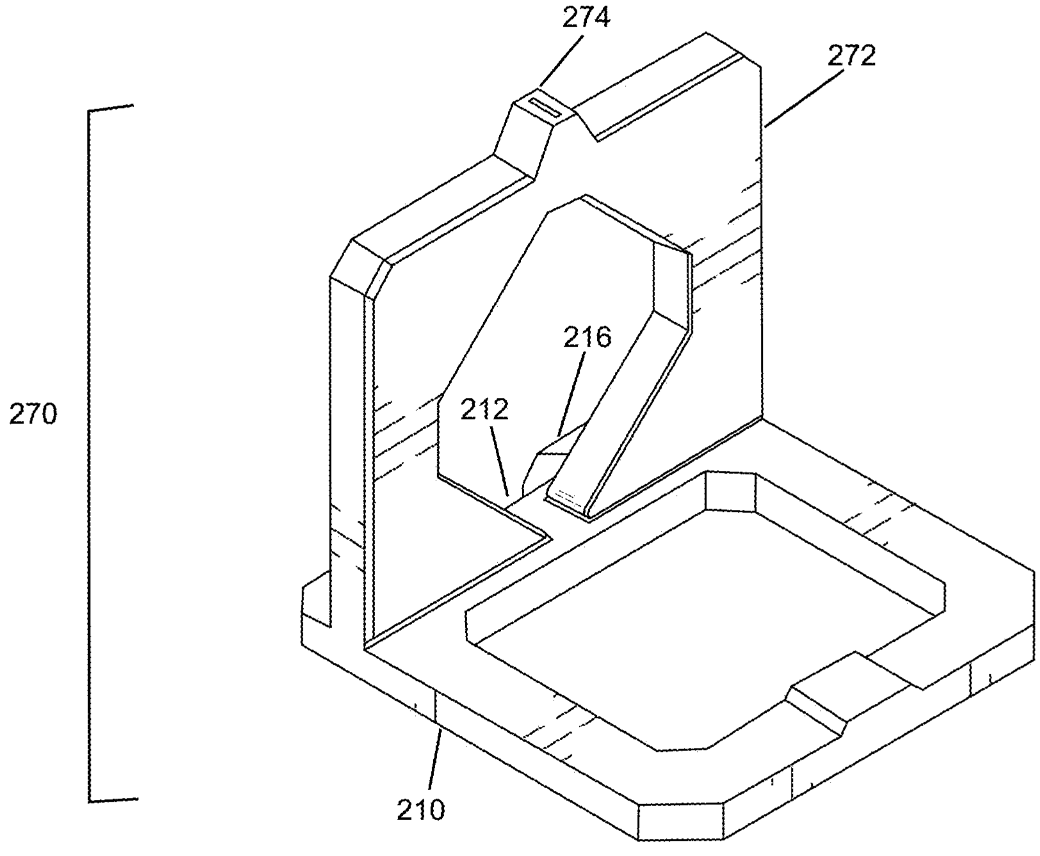
FIG. 4 is an isometric view of a CT phantom jig consistent with certain embodiments of the present invention.

Turning now to FIG. 4, the figure presents a CT phantom jig 270 consistent with certain embodiments of the present invention. In an exemplary embodiment, due to the size of the cylindrical phantom that the CT phantom jig 270 supports, the CT phantom jig 270 may comprise a jig-to-jig interface 212 at only one end. The jig-to-jig interface 212 of a base 210 of the CT phantom jig 270 may comprise a dovetail notch 216. In alternative embodiments of the CT phantom jig 270, the jig-to-jig interface 212 may be a dovetail tab. The jig-to-jig interface 212 is a coupling to an adjacent jig that enables the placement of multiple interconnected phantoms on the treatment couch simultaneously. The CT phantom jig 270 comprises a vertical support wall 272 that projects upwards from the base 210 and is laterally oriented. The cylindrical calibration phantom may hang onto the top of the vertical support wall 272 using hooks that are a part of the phantom. The cylindrical phantom may extend longitudinally away from the dovetail notch 216 and may therefore prevent placing any other phantom opposite the dovetail notch 216 as part of a daisy chain that includes the CT phantom jig 270. A centering stub 274 may prevent the cylindrical phantom from sliding off of the CT phantom jig 270 in a lateral direction by limiting lateral movement of the hooks located on the phantom.

Figure 5:
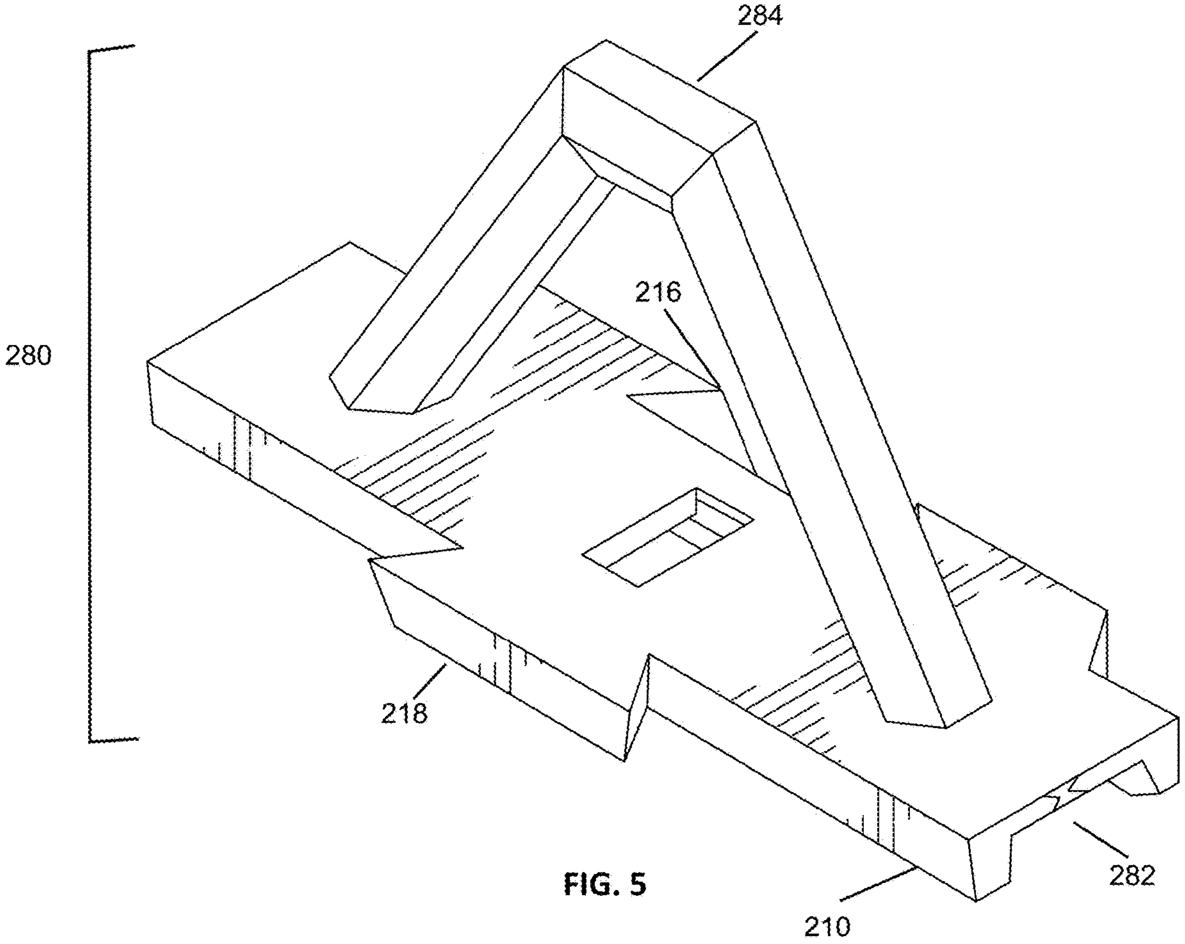
FIG. 5 is an isometric view of an adapter jig consistent with certain embodiments of the present invention.

Turning now to FIG. 5, the figure presents an adapter jig 280 consistent with certain embodiments of the present invention. In an exemplary embodiment, jig-to-jig interfaces of a base 210 of the adapter jig 280 comprise a dovetail notch 216 and a dovetail tab 218. The jig-to-jig interfaces 212 are couplings between multiple jigs that enable the placement of multiple interconnected phantoms on the treatment couch simultaneously. The adapter jig 280 may rest on an index bar that may be coupled to the treatment couch such that the index bar passes under the adapter jig 280 through an index bar coupler 282. The index bar may be laterally oriented on the treatment couch so that the dovetail notch 216 and the dovetail tab 218 are positioned at the longitudinal ends of the adapter jig 280. Up to two additional calibration phantoms may couple to the adapter jig 280 on either or both ends of the adapter jig 280. Other jigs may also couple to the ends of the additional phantoms to form a daisy chain of jigs that extend longitudinally along the treatment couch. All of the interconnected jigs may be localized with respect to a reference position established by the index bar via the intervention of the adapter jig 280. The adapter jig 280 may comprise a handle 284 for lifting.

Figure 6:
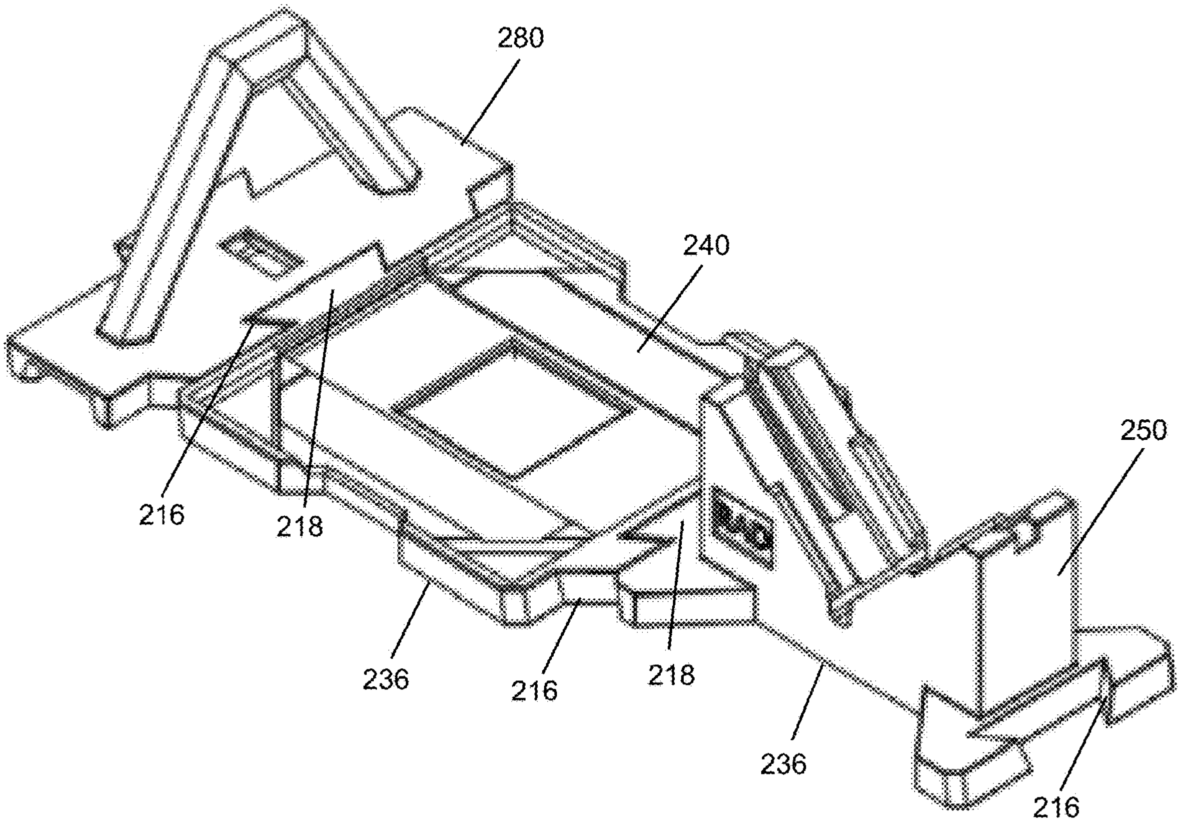
FIG. 6 is an isometric view of a plurality of carrier jigs consistent with certain embodiments of the present invention, illustrating interconnection of the jigs to form a daisy chain.

Turning now to FIG. 6, the figure presents a plurality of carrier jigs and an adapter jig 280 interconnected to each other consistent with certain embodiments of the present invention. In an exemplary embodiment, a multi-phantom jig 240 located at the center of a daisy chain is coupled at one end to an angled jig 250 and at the opposite end to the adapter jig 280. The plurality of carrier jigs may interconnect to each other and to the adapter jig 280 when a dovetail notch 216 on a first jig 236 engages a dovetail tab 218 on a second jig 236. In FIG. 6, the dovetail notch 216 on the multi-phantom jig 240 is coupled to the dovetail tab 218 on the angled jig 250. Similarly, the dovetail tab 218 on the multi-phantom jig 240 is coupled to the dovetail notch 216 on the adapter jig 280.

Figure 7:
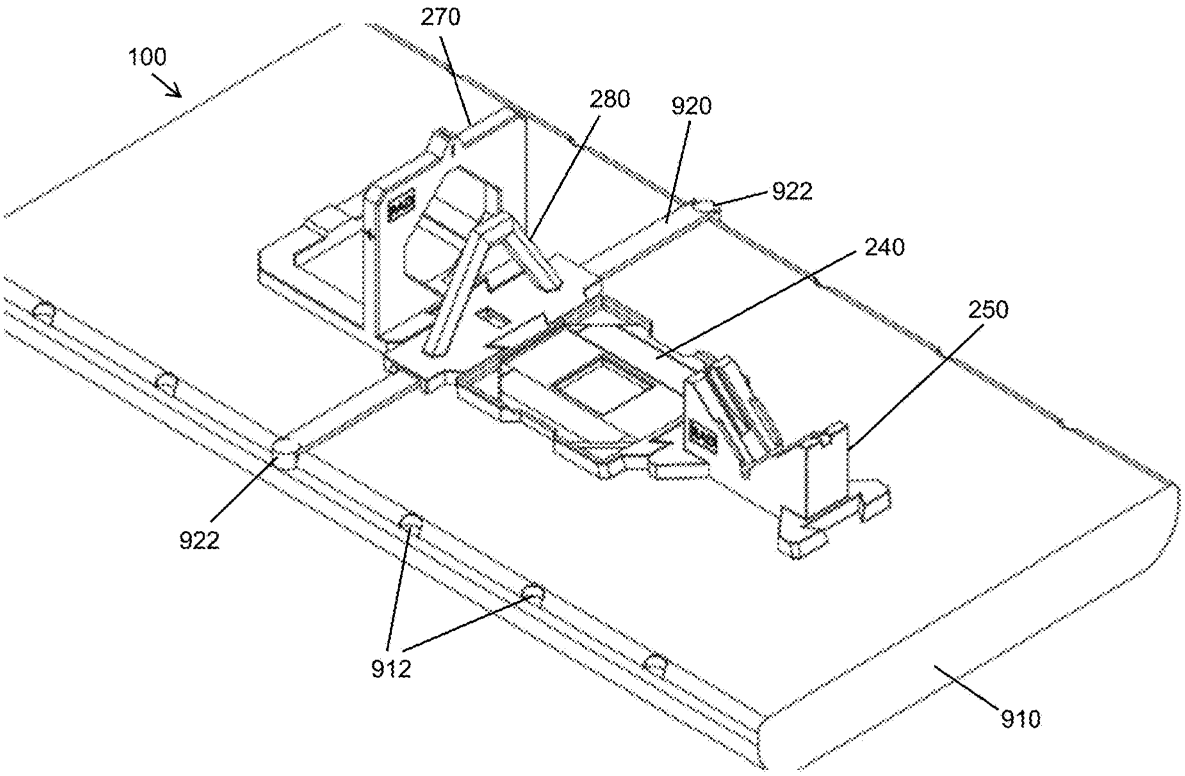
FIG. 7 is an isometric view of a plurality of carrier jigs and an adapter jig consistent with certain embodiments of the present invention, illustrating localization of positioning established by the coupling of the adapter jig and the index bar on the treatment couch.

Turning now to FIG. 7, the figure presents a plurality of carrier jigs and an adapter jig 280 interconnected to each other and positioned at a fixed location relative to a treatment couch 910 consistent with certain embodiments of the present invention. In an exemplary embodiment, an adapter jig 280 in a daisy chain comprising a CT phantom jig 270, the adapter jig 280, a multi-phantom jig 240, and the angled jig 250 is coupled to an index bar 920 at a reference location on the treatment couch 910. The reference location is established by coupling feet 922 located at the ends of the index bar 920 into positioning cutouts 912 spaced along the sides of the treatment couch 910. The invention 100 enables a medical physicist to position multiple calibration phantoms on the plurality of carrier jigs which are interconnected and held at fixed reference positions relative to the treatment couch 910. The multiple calibration phantoms, when so arranged, may then be measured during one trip out of a radiation oncology treatment vault.

While certain illustrative embodiments have been described, it is evident that many alternatives, modifications, permutations and variations will become apparent to those skilled in the art in light of the foregoing description.

What is claimed is:

1. A carrier jig comprising a base portion, said carrier jig having one or more jig-to-jig interfaces, and one or more positioning assistants;

each of said one or more positioning assistants operable to position and retain a calibration phantom at fixed reference locations relative to a treatment couch;

where the carrier jig is attached to said treatment couch and placed within a treatment area of a medical imaging system;

where the one or more positioning assistants of said carrier jig support and orient a calibration phantom while the calibration phantom is imaged;

where any of said one or more jig-to-jig interfaces are operable to couple the carrier jig to one or more adjacent carrier jigs.

2. The carrier jig according to claim 1 where two or more of said one or more carrier jigs are coupled to form a connected chain of carrier jigs such that multiple calibration phantoms are imaged in a single imaging operation without physical intervention.

3. The carrier jig according to claim 1 where the one or more jig-to-jig interfaces are operable to couple a first jig to a subsequent jig through attachment of a connection tab formed on the exterior surface of each of said jig-to-jig interfaces;

where said connection tab of the first jig interlocks with a connection tab of the subsequent jig to couple the first jig to said subsequent jig to create a chain of jigs forming a carrier jig chain.

4. The carrier jig according to claim 3 where said carrier jig chain comprises a chain of carrier jigs where the first jig is a carrier jig; and where a subsequent connected jig is selected from a group of carrier jigs each of which is configured to support and orient phantoms having differing physical shape and density and/or an adapter jig.

5. The carrier jig according to claim 1 where the carrier jig chain is a multi-phantom jig;

where the one or more positioning assistants of the multi-phantom jig comprise a plurality of side walls, a plurality of corner supports, and one or more central depressions formed of static, natural depressions in the body of each of said carrier jigs within said carrier jig chain;

where each carrier jig within the multi-phantom jig is configured to support a calibration phantom by retaining the calibration phantom within the plurality of side walls, the plurality of corner supports, the one or more central depressions, or any combination thereof when the calibration phantom is positioned within the static, natural depressions of each carrier jig of the multi-phantom jig.

6. A carrier jig system comprising a plurality of carrier jigs, each carrier jig having one or more jig-to-jig interfaces and one or more positioning assistants;

where the plurality of carrier jigs are placed on a treatment couch of a medical imaging system;

where the plurality of carrier jigs are interconnected via said jig-to-jig interfaces that couple adjacent jigs to form a carrier jig chain;

where said carrier jig chain retains a calibration phantom within each jig of said carrier jig chain;

where said one or more positioning assistants position and retain said carrier jig chain at fixed reference locations relative to a treatment couch;

where the plurality of carrier jigs are operable to support and orient said calibration phantoms while the calibration phantoms are imaged;

where the treatment couch is repositioned along said carrier jig chain so as to move to each calibration phantom retained within said carrier jig chain.

7. The system according to claim 6 where the said carrier jig chain is removably coupled to an index bar;

where the index bar is removably coupled to the treatment couch;

where said carrier jig chain fixes the positions of the plurality of carrier jigs at reference locations relative to the treatment couch.

8. The system according to claim 6, further comprising:

said carrier jig chain comprises a chain of carrier jigs where the first jig in said carrier jig chain is selected from a group of any of a plurality of carrier jigs; and where a subsequent connected jig attached to said first carrier jig is selected from a group including any of a plurality of carrier jigs and/or an adapter jig; and where said carrier jig chain comprises one or more carrier jigs and an adapter jig.

* * * * *